United States Patent [19]

Schnurr et al.

[11] Patent Number: 5,827,938
[45] Date of Patent: Oct. 27, 1998

[54] PREPARATION OF AMINES AND AMINONITRILES

[75] Inventors: Werner Schnurr, Herxheim; Guido Voit, Schriesheim; Klemens Flick, Herxheim; Johann-Peter Melder, Neuhofen; Rolf-Hartmuth Fischer, Heidelberg; Wolfgang Harder, Weinheim, all of Germany

[73] Assignee: BASF Aktiengesellschaft, Ludwigshafen, Germany

[21] Appl. No.: 635,684

[22] Filed: Apr. 22, 1996

[30] Foreign Application Priority Data

Apr. 10, 1996 [DE] Germany .................. 196 14 154.0

[51] Int. Cl.⁶ .................................................. C07C 255/00
[52] U.S. Cl. ............................................. 558/459; 558/459
[58] Field of Search ............................................... 558/459

[56] References Cited

U.S. PATENT DOCUMENTS 5,557,004  9/1996  Flick et al. .

*Primary Examiner*—Johann Richter
*Assistant Examiner*—Joseph Murray
*Attorney, Agent, or Firm*—Keil & Weinkauf

[57] ABSTRACT

A process for the coproduction of 6-aminocapronitrile (ACN) and hexamethylenediamine (HMD) by treatment of adiponitrile (ADN) with hydrogen in the presence of a nickel-containing catalyst at temperatures not below room temperature and elevated hydrogen partial pressure in the presence or absence of a solvent comprises, after the conversion based on ADN and/or the selectivity based on ACN has or have dropped below a defined value (a) interrupting the treatment of ADN with hydrogen by stopping the feed of ADN and of the solvent, if used, (b) treating the catalyst at from 150° to 400° C. with hydrogen using a hydrogen pressure within the range from 0.1 to 30 MPa and a treatment time within the range from 2 to 48 h, and (c) then continuing the hydrogenation of ADN with the treated catalyst of stage (b).

4 Claims, No Drawings

PREPARATION OF AMINES AND AMINONITRILES

BACKGROUND OF THE INVENTION

1. Field of the Invention

The present invention relates to an improved process for the coproduction of 6-aminocapronitrile (ACN) and hexamethylenediamine (HMD) by treatment of adiponitrile (ADN) with hydrogen in the presence of a nickel-containing catalyst at temperatures not below room temperature and elevated hydrogen partial pressure in the presence or absence of a solvent.

The present invention further relates to a process wherein the treatment of ADN is carried out in suspension or in a fixed bed in a downflow or outflow process.

2. Description of the Related Art

The hydrogenation of ADN to 6-aminocapronitrile in the presence of solvents, especially ammonia, and nickel-containing catalysts has been described in detail for example in U.S. Pat. No. 2,762,835, U.S. Pat. No. 2,208,598 and WO 92/21650.

The nickel-containing catalysts used in the hydrogenation of ADN lose activity in long runs and therefore have to be replaced with new catalysts once the activity has dropped below a certain value.

Nickel-containing catalysts are widely used in industry for steam reforming, for methanization and for the hydrogenation of functional groups such as CO double bonds, C—C multiple bonds or nitrile groups. In many of the aforementioned applications the catalyst is deactivated sooner or later through the formation of carbonaceous deposits on the active catalyst surface. The formation of carbonaceous deposits in steam reforming and the removal of these layers by reaction with oxygen, hydrogen, steam or carbon dioxide is described in Trimm, Catal. Rev.Sci. Eng., 16(2), 155–187 (1977). Measurable reaction rates are achieved with hydrogen only at temperatures above 550° C.

The regeneration of catalysts coated with carbonaceous deposits is generally effected by burning off the organic coatings with nitrogen-air mixtures. However, this method can be used only with catalysts which remain stable on reaction with air supported catalysts with a stable structure of oxidic material, such as $SiO_2$, $Al_2O_3$, $TiO_2$, can be successfully regenerated by this method. For instance, GB-A 2,284,163 describes the regeneration of a supported catalyst with Pt, Pd, Ru, Rh, etc. or nickel by treatment of a gas containing at least chlorine and oxygen.

Catalysts with very high metal contents become damaged on burning off the organic deposits with air, altering their mechanical properties (see EP-A 61,042).

EP-A 61,042 also discloses that nickel-containing catalysts having a maximum nickel content of 50% by weight for the hydrogenation of butynediol to butanediol can be regenerated by hydrogen treatment at temperatures between 200° and 500° C., preferably at temperatures above 275° C.

Similarly, U.S. Pat. No. 5,310,713 describes a regeneration with hydrogen for an alkylation catalyst which may contain nickel, but the regeneration with hydrogen is carried out in the presence of liquid alkane and of a chloride source.

It is known from Journal of Catalysis 143 (1993), 187–200, that a nickel catalyst (25% by weight of Ni on $SiO_2$) which is used for the hydrogenation of acetonitrile in the gas phase can be regenerated by treatment with hydrogen at temperatures of above 200° C.

The cited references do not reveal whether it is also possible to regenerate nickel-containing catalysts used in the hydrogenation of higher boiling dinitriles, especially adiponitrile. For bifunctional compounds such as dinitriles, in particular, can give rise, under reaction conditions, to the formation of oligomers which lead to regeneration problems.

SUMMARY OF THE INVENTION

It is an object of the present invention to provide a process whereby it is possible to regenerate the nickel-containing catalysts used in hydrogenation of ADN to ACN and HMD in a simple way, without incurring long shutdown times during the regeneration of the catalysts. More particularly, the object is to raise catalyst activity in respect of conversion and selectivity in the hydrogenation of ADN as closely as possible to the level of the unused catalyst.

We have found that these objects are achieved by a process for the coproduction of 6-aminocapronitrile (ACN) and hexamethylenediamine (HMD) by treatment of adiponitrile (ADN) with hydrogen in the presence of a nickel-containing catalyst at temperatures not below room temperature and elevated hydrogen partial pressure in the presence or absence of a solvents which comprises, after the conversion based on ADN and/or the selectivity based on ACN has or have dropped below a defined value (a) interrupting the treatment of ADN with hydrogen by stopping the feed of ADN and of the solvent, if used, (b) treating the catalyst at from 150° to 400° C. with hydrogen using a hydrogen pressure within the range from 0.1 to 30 MPa and a treatment time within the range from 2 to 48 h, and (c) then continuing the hydrogenation of ADN with the treated catalyst of stage (b).

DESCRIPTION OF THE PREFERRED EMBODIMENTS

The nickel catalysts used can be customary Raney nickel catalysts (as fixed-bed or suspension catalysts) or supported catalysts. Raney nickel catalysts are known and commercially available or preparable in a known manner from a nickel-aluminum alloy by treatment with a base such as sodium hydroxide solution. The support used may typically be alumina, silica, activated carbons, titania and zirconia. Supported catalysts customarily have a nickel content within the range from 3 to 95, preferably 20 to 95, especially from 50 to 95, % by weight, based on the total mass of nickel and support.

The catalysts may also be modified, if desired, with metals of group VIB (Cr, Mo, W) and VIII of the periodic table (Fe, Ru, Os, Co, Rh, Ir, Pd, Pt) and also with copper, rhenium or manganese, in which case the nickel content of the catalyst is generally within the range from 50 to 99.9, preferably from 80 to 99, % by weight, based on the active components (nickel+modifier).

Furthermore, the catalysts may be modified with a compound based on an alkali metal or an alkaline earth metal such as lithium, sodium, potassium, rubidium, cesium, magnesium, calcium, strontium and barium, especially cesium. It is customary to use a weight ratio within the range from 0 to 5, preferably from 0.1 to 3, % by weight of alkali metal or alkaline earth metal to nickel.

The nickel catalysts usable according to the invention may be prepared in various ways. The preparation of supported nickel catalysts is customarily effected by impregnating a ceramic support with an aqueous organic solution of a nickel salt and, if desired, the modifier, then drying and calcining in a conventional manner. The solubility of the salts and pore volume of the support limits, according to observations to date, the amount of nickel which can be applied by one impregnating step, so that, if desired, the impregnating procedure may have to be repeated more than once, in which case, in general, the catalyst is dried and calcined after each impregnating step in order that the desired level of nickel may be obtained on the catalyst. It is also possible to apply nickel by precipitation of a sparingly soluble nickel compound such as the corresponding hydroxide or carbonate compound to a support suspended in the precipitation solution. The precipitates can be shaped in a conventional manner, customarily after filtration or spray drying.

The hydrogenations can be carried out with preference in upflow, downflow or suspension processes.

When the reaction is carried out in a suspension, it is customary to choose temperatures within the range from 40° to 150° C., preferably within the range from 50° to 10° C., particularly preferably within the range from 60° to 90° C.; the pressure is generally chosen to be within the range from 2 to 20, preferably 3 to 10, particularly preferably from 4 to 9, MPa. The residence times are essentially dependent on the desired yield, selectivity and the desired conversion; customarily, the residence time is selected so as to maximize the yield, for example within the range from 50 to 275, preferably within the range from 70 to 200, min.

In the suspension process, the solvent used is preferably ammonia, amines, diamines and triamines having from 1 to 6 carbon atoms such as trimethylamine, triethylamine, tripropylamine and tributylamine or alcohols, especially methanol and ethanol, particularly preferably ammonia. It is advantageous to use a dinitrile concentration within the range from 10 to 90, preferably from 30 to 80, particularly preferably from 40 to 70, % by weight, based on the sum of dinitrile and solvent.

The amount of catalyst used is generally within the range from 1 to 50, preferably from 5 to 20, % by weight, based on the amount of dinitrile used.

The suspension hydrogenation can be carried out batchwise or, preferably, continuously, generally in the liquid phase.

The hydrogenation may also be carried out batchwise or continuously in a downflow or upflow process in a fixed-bed reactor, in which case it is customary to employ a temperature within the range from 20° to 150° C., preferably within the range from 30° to 90° C., and a pressure generally within the range from 2 to 30, preferably within the range from. 3 to 20, MPa. The hydrogenation is preferably carried out in the presence of a solvent, preferably ammonia, amines, diamines and triamines having from 1 to 6 carbon atoms such as trimethylamine, triethylamine, tripropylamine and tributylamine or alcohol, preferably methanol and ethanol, particularly preferably ammonia. In a preferred embodiment, the amount of ammonia used is within the range from 0.5 to 10, preferably from 1 to 6, g per g of adiponitrile. Preference is given to using a catalyst space velocity within the range from 0.1 to 2.0, preferably from 0.3 to 1.0, kg of adiponitrile/l*h. Here too it is possible to adjust the conversion and hence the selectivity in a specific manner by varying the residence time.

The hydrogenation can be carried out in a customary suitable reactor.

If the reaction is carried out in the gas phase, it is customary to use temperatures within the range from 100° to 250° C., preferably within the range from 160° to 200° C.; the pressure employed is generally within the range from 0.01 to 3, preferably from 0.09 to 0.5, MPa. Furthermore, the molar ratio of hydrogen to ADN is generally within the range from 2:1 to 300:1, preferably within the range from 10:1 to 200:1.

In a preferred embodiment, the hydrogenation of ADN is carried out in the presence of ammonia as solvent using fixed-bed catalysts as described above by a process wherein, following the deactivation of the catalyst, ie. a decrease in the conversion of ADN and/or selectivity based on ACN below a defined value, first the feed of adiponitrile and ammonia is switched off, then the temperature is brought to 200°–250° C., and subsequently the catalyst is treated for from five to six hours with from 200 to 800, preferably from 500 to 700, especially 600, l of hydrogen/l of cat.×h. Thereafter the temperature is customarily brought back down to reaction temperature and the hydrogenation is continued.

Prior to starting the regeneration, it is preferable to remove the hydrogenation mixture still present in the reactor. It may further be advantageous, especially if the treatment of the ADN with hydrogen is carried out in suspension, to wash the catalyst before the actual regeneration, ie. after interruption of the treatment of ADN with hydrogen (stage (a)) and before treatment with hydrogen (stage (b)), with the solvent present in the system, especially with liquid ammonia. The wash temperature employed is customarily within the range from 20° to 200° C., especially within the range from 20° to 100° C. It is generally advantageous to carry on the wash for a period of from 2 to 24 hours.

From experience to date, the regeneration can be carried out at any desired time. From an economic point of view, a regeneration appears to be sensible when the conversion based on ADN and/or the selectivity based on ACN has dropped by more than 10%, based on the initial value.

According to the invention, the regeneration of the catalyst is carried out at temperatures within the range from 150° to 400° C., preferably within the range from 180° to 270° C., especially within the range from 200° to 250° C., using a hydrogen pressure within the range from 0.1 to 30 MPa, preferably within the range from 0,1 to 20 MPa, and a treatment time within the range from 2 to 48 h, preferably within the range from 2 to 24 h. A continuous process is customarily carried out with the hydrogen rate within the range from 100 to 1500, preferably within the range from 200 to 1000, l of hydrogen/l of reactor volume×hour.

The process of the invention makes it possible to achieve distinct improvements in the life and space-time yield of nickel catalysts in the hydrogenation of adiponitrile to 6-aminocapronitrile and hexamethylenediamine (nylon 6 and nylon 66 intermediates).

EXAMPLES

Example 1

(Suspension Hydrogenation)

Reactor: 250 ml autoclave with sampling port (material of construction: HC 4); agitation by disk stirrer.

Batch: in each case 48 g of ADN, 5.6 g of Raney nickel (BASF, H 1–50, water-moist).

Raney nickel was introduced into an autoclave under a protective gas (argon). The autoclave was then sealed and 150 ml of liquid $NH_3$ were injected. After brief stirring, the bulk of the ammonia was pressed out of the reactor via a riser pipe equipped with a frit. This process was repeated six times with 50 ml of liquid ammonia each time to obtain anhydrous Raney nickel as a representative starter catalyst (ammonia holdup about 100 ml). Thereafter the system was heated to 80° C., 48 g of adiponitrile were metered in, and the pressure was raised with hydrogen to 7 MPa. Catalyst-free samples of the liquid phase were removed through the sampling port after 20, 45, 90, 135, 180 and 225 min.

After 225 min, the temperature in the reactor was reduced to 25° C. and the catalyst-free reaction mixture was removed. The catalyst remaining in the reactor was rinsed six times with 50 ml of liquid ammonia each time, at room temperature, by the method described for the wash prior to the first use. For the subsequent run the system was heated back up to 80° C. and the reactants were metered in afresh. The runs with sampling and washing were repeated a number of times.

Table 1 shows the conversion of the adiponitrile and the selectivity to 6-aminocapronitrile as evident from the GC data after a hydrogenation time of 225 min. Apart from ACN, hexamethylenediamine was formed almost exclusively.

TABLE 1

| Run | ADN conversion | ACN selectivity |
|---|---|---|
| 1 | 84.2 | 59.6 |
| 2 | 49.6 | 70.4 |
| 3 | 43.4 | 64.7 |
| 4 | 37.3 | 70.1 |
| 5 | 30.6 | 75.2 |
| 6 | 29.2 | 75.2 |
| 7 | 26.3 | 77.2 |
| 8 | 24.2 | 80.0 |
| 9 | 17.3 | 79.5 |
| 10 | 16.2 | 85.0 |
| 11 | 13.2 | 81.6 |
| 12 | 9.0 | 86.8 |
| 13 | 7.4 | 95.3 |
| 14 | 6.0 | 85.5 |
| 15 | 5.3 | 84.6 |
| 16 | 5.4 | 87.2 |
| 17 | 4.9 | 90.3 |
| 18 | 5.8 | 88.2 |

Following run 18, the hydrogenation mixture was removed and the deactivated catalyst was rinsed six times with liquid ammonia. Thereafter the ammonia was completely decompressed and entirely displaced from the reactor using argon. The reactor was then heated to 100° C. and once more flushed with argon. The argon was then displaced by flushing with hydrogen. The reactor was then heated to 250° C. and the pressure set with hydrogen to 10 MPa. The reactor was left at 250° C. for 5 hours. The autoclave was then heated down to room temperature, the gas-phase was completely decompressed, and the next block of runs was started.

TABLE 2

| Run after regeneration of catalyst | | |
|---|---|---|
| Run | ADN conversion | ACN selectivity |
| 19 | 54.9 | 80.5 |

Regeneration with hydrogen made it possible to raise the conversion based on ADN from 5.8% to 54.9%.

Example 2
(Continuous Gas Phase Hydrogenation)
Catalyst Preparation 4 mm $Al_2O_3$ extrudates (SPH 512 B, Rhône Poulenc) were initially impregnated for two hours at room temperature with an aqueous, 3.5% strength by weight $CsNO_3$ solution, then air-dried at 120° C. for 16 h and subsequently calcined in air at 350° C. over 4 h. The extrudates thus calcined were then impregnated with an aqueous, 44.3% strength by weight $Ni(NO_3)_2$ solution for 2 h, then air-dried at 120° C. for 16 h and subsequently calcined in air at 350° C. over 4 h. Thereafter the impregnation, drying and calcining was repeated with the nickel salt solution.

After cooling, the extrudates were installed in a reduction apparatus and flushed for 2 h at room temperature with 20 l/h of $N_2$ to remove air. This was followed by heating to 300° C. with a heating rate of 2° C./min and a hydrogen flow of 20 l/h of $H_2$ and the 300° C. were maintained for 2 h.

The catalyst thus prepared contained 0.1% by weight of Cs and 13% by weight of Ni, based on the total weight of the extrudates.

Hydrogenation 40 g/h of adiponitrile were introduced into a vaporizer (280° C.) and passed from there with 400 /h of hydrogen through a tubular reactor (packed with 330 g of catalyst; reactor dimensions: length=2000 mm, diameter=15 mm) in the downflow direction. The reactor temperature was 180° C. The gaseous reactor effluent was condensed in cold traps and analyzed by gas chromatography. Following a startup phase, the adiponitrile conversion obtained was 45.2%, which dropped to 24.1% over a period of 445 h. The aminocapronitrile selectivity was within the range from 80 to 90%.

The dinitrile feed was then turned off and the catalyst regenerated in the reactor with 200 l/h of hydrogen at 250° C. over 6 hours. Following renewed startup under identical conditions (see above), a conversion of 42.7% was obtained; that is, the catalyst had almost been restored to its initial activity.

Example 3
(Fixed-Bed Hydrogenation in the Liquid Phase)
Catalyst Preparation 2.5 kg of an NiAl alloy (from BASF, H1-55) were impregnated at 80° C. with stearic acid. After comminution of the cooled and solidified mass, the powder obtained was pressed into tablets (3 mm height, 3 mm diameter). The tablets thus obtained were then calcined at 900° C. over 2 h. The activation of the tablets was carried out with sodium hydroxide solution. For this, 2.4 kg of the tablets were introduced into 5.7 l of water and then admixed with vigorous stirring to a total of 1.44 kg of NaOH platelets. On completion of the addition the stirring was continued at 90° C. for a further 24 h. After cooling, the activated tablets were washed with water until the wash liquor was pH-neutral.

The activated catalyst tablets were installed in the reactor under water and rinsed with ammonia.

Hydrogenation 370 g/h of adiponitrile and 1.1 kg/h of ammonia were passed with 500 l/h of hydrogen through a tubular reactor (packed with 740 ml of catalyst; length=1800 mm, diameter 30 mm) in the upflow direction. The reactor temperature was 50° C., the pressure was 20 MPa. The reactor effluent was analyzed by gas chromatography. Following a startup phase an adiponitrile conversion of 45% was obtained, which dropped to 20% over a period of 280 hours. The aminocapronitrile selectivity rose from initially 80 to 90%.

The dinitrile and ammonia feed were then switched off and the catalyst regenerated in the reactor at 200° C. and a hydrogen pressure of 20 MPa (at 500 l/h of hydrogen) for 5 hours. After renewed startup under identical conditions (see above) the conversion rose to 45% (at an ACN selectivity of 80%); that is, the catalyst had been restored to its initial activity.

We claim:

1. In a process for the coproduction of 6-aminocapronitrile (ACN) and hexamethylenediamine (HMD) by the hydrogenation of adiponitrile (ADN) to convert ADN to both ACN and HMD, said hydrogenation taking place at a temperature of from 40° to 150° C. at a hydrogen partial pressure of from 2 to 20 MPa in the optional presence of a solvent or the hydrogenation takes place in a fixed bed reactor in a downflow or upflow process at from 20° to 150° C. and at a pressure of from 2 to 30 MPa, the improvement which comprises: continuing the conversion of ADN to ACN and HMD until the conversion of ADN has dropped below a pre-determined value or until the selective conversion to ACN has dropped below a pre-determined value, and thereafter (a) interrupting the hydrogenation of ADN by stopping the feed of ADN and of the solvent, if used, (b) treating the catalyst at from 150° to 400° C. with hydrogen using a hydrogen pressure within the range from 0.1 to 30 MPa and a treatment time within the range from 2 to 48 h, and (c) then continuing the hydrogenation of ADN with the treated catalyst of stage (b).

2. The process of claim 1, wherein the treatment of ADN with hydrogen is carried out in suspension at a temperature within the range from 50° to 100° C. and a pressure within the range from 3 to 10 MPa.

3. The process of claim 1, wherein the treatment of ADN with hydrogen is carried out in a fixed-bed reactor in a downflow or upflow process at a temperature within the range from 20° to 150° C. and a pressure within the range from 2 to 30 MPa.

4. The process of claim 2, wherein, following interruption of the treatment of ADN with hydrogen (stage (a)) and before the treatment of the catalyst with hydrogen (stage (b)), the catalyst is rinsed with liquid ammonia and, after the rinse, the ammonia is displaced with an inert gas.

* * * * *

UNITED STATES PATENT AND TRADEMARK OFFICE
CERTIFICATE OF CORRECTION

PATENT NO.: 5,827,938

DATED: October 27, 1998

INVENTOR(S): SCHNURR et al.

It is certified that error appears in the above-identified patent and that said Letters Patent is hereby corrected as shown below:

```
The title should read --  PROCESS FOR COPRODUCING 6-
AMINOCAPRONITRILE AND 6-HEXAMETHYLENEDIAMINE--.
```

Signed and Sealed this

Twenty-ninth Day of August, 2000

Attest:

Q. TODD DICKINSON

*Attesting Officer*     *Director of Patents and Trademarks*